United States Patent

Koch et al.

[11] Patent Number: 6,066,755
[45] Date of Patent: May 23, 2000

[54] AMPHIPHILIC COMPOUNDS WITH A PLURALITY OF HYDROPHILIC AND HYDROPHOBIC GROUPS BASED ON CARBONIC ACID DERIVATIVES

[75] Inventors: Herbert Koch, Raesfeld; Klaus Kwetkat, Lünen, both of Germany

[73] Assignee: Huels Aktiengesellschaft, Marl, Germany

[21] Appl. No.: 09/091,411

[22] PCT Filed: Nov. 14, 1996

[86] PCT No.: PCT/EP96/04979

§ 371 Date: Jun. 22, 1998

§ 102(e) Date: Jun. 22, 1998

[87] PCT Pub. No.: WO97/22577

PCT Pub. Date: Jun. 26, 1997

[30] Foreign Application Priority Data

Dec. 20, 1995 [DE] Germany .................. 195 47 643

[51] Int. Cl.⁷ .................................................. C07C 69/96
[52] U.S. Cl. .................. 558/266; 252/8.81; 252/351; 508/552; 510/119; 510/130; 510/235; 510/332; 510/499
[58] Field of Search ..................... 558/263, 266

[56] References Cited

U.S. PATENT DOCUMENTS 5,160,450  11/1992  Okahara et al. .
5,723,590   3/1998  Koch et al. .

FOREIGN PATENT DOCUMENTS 0353503  2/1990  European Pat. Off. .

OTHER PUBLICATIONS

Derwent Abstract No. 92–189237, Derwent Information Ltd.; JP 04–124165, Sep. 12, 1990, abstract.
Chemical Abstract, vol. 101, No. 12, Sep. 17, (1984), p. 89 abstract No. 92741; Takemoto Oil and Fat Co., Ltd, "Lubricant finishes for synthetic fibers".

R. Zana, M. Benrraou, R. Rueff, Langmuir, 7 (1991) 1072–1075.
R. Zana, Y. Talmon, Nature, 362 (1993) 228.
E. Alami, G. Beinert, P. Marie, R. Zana, Langmuir, 9 (1993) 1465–1467.

*Primary Examiner*—Michael G. Ambrose
*Attorney, Agent, or Firm*—Oblon, Spivak, McClelland, Maier & Neustadt, P.C.

[57] ABSTRACT

The invention relates to amphiphilic compounds of the general formula I

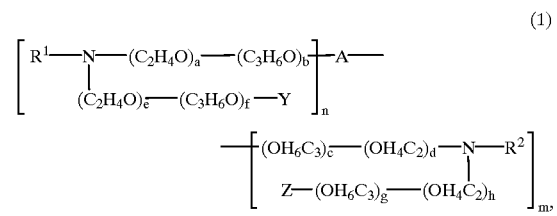

which have at least two hydrophilic and at least two hydrophobic groups and are based on carbonic acid derivatives.

The spacer A is an aliphatic, cyclic or acyclic or an aromatic di-, oligo- or polycarbonate of the formula II:

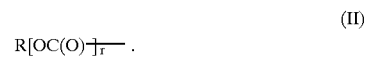

The amphiphilic compounds according to this invention are mostly surface-active and are suitable as emulsifiers, demulsifiers, detergents, dispersants and hydrotropes for industrial and domestic use, in particular in the fields of metalworking, ore extraction, surface finishing, plastics processing, washing and cleaning, cleaning of hard surfaces, manual dishwashing compositions, cosmetics, medicine and food processing and preparation.

20 Claims, No Drawings

AMPHIPHILIC COMPOUNDS WITH A PLURALITY OF HYDROPHILIC AND HYDROPHOBIC GROUPS BASED ON CARBONIC ACID DERIVATIVES

This application is a 371 of PCT/EP96/04979 filed Nov. 14, 1996.

The invention relates to amphiphilic compounds containing a plurality of hydrophilic and hydrophobic groups, based on carbonic acid derivatives.

Known amphiphilic substances encompass a wide variety of anionic, cationic, nonionic and zwitterionic compounds. By far the majority of these substances consist of a hydrophilic head group and at least one hydrophobic part.

With amphiphilic substances there is a need, for ecological reasons, for example reduction packaging and transportation, to achieve an increasingly greater effect per unit mass of substance employed. Since optimization by mixing amphiphilic substances produces only very limited advances, novel amphiphilic substances with greater effectiveness are required. It is therefore necessary in particular to find substances with lower critical micelle concentrations and/or lower surface tensions in order to be able to reduce markedly the amounts of active substance employed. Initial approaches to a solution in the direction of higher-performance amphiphilic substances by doubling one part of the structure (hydrophilic head group, hydrophobic group) are already known. Thus, cationic surface-active compounds can be obtained by adding long-chain alkyl halides onto permethylated alkylenediamines [R. Zana, M. Benrraou, R. Rueff, Langmuir, 7 (1991)1072; R. Zana, Y. Talmon, Nature, 362 (1993) 228; E. Alami, G. Beinert, P. Marie, R. Zana, Langmuir, 9 (1993) 1465].

Anionic surface-active compounds containing at least two hydrophilic groups and at least two hydrophobic groups have to date been prepared only on the basis of diglycidyl ethers (U.S. Pat. No. 5,160,450, JP 01 304 033, JP 4 124 165). However, diglycidyl ethers are regarded as toxicologically objectionable and are rather costly. Furthermore, epichlorohydrin is used for their preparation, which leads to large amounts of residues so that these compounds are no longer up to date from ecotoxicological and economic viewpoints.

The object was therefore to find amphiphilic compounds which have at least two hydrophilic groups and at least two hydrophobic groups, are very effective relative to the amount used, and furthermore can be prepared from raw materials which are readily available industrially and without large amounts of unwanted by-products being formed. In addition, the compounds should be easy to cleave again.

The object is achieved according to the invention by amphiphilic di-, oligo- or polycarbonates whose basic skeleton can be prepared from di-, oligo- or polycarbonic acid derivatives and alkoxylated fatty amines and fatty acid amides. The corresponding di-, oligo- or polycarbonates are nonionic surfactants which, nevertheless, can be further reacted to give anionic amphiphilic compounds. In this context, suitable reactions are sulfonation, carboxymethylation and conversion to, for example, isethionates, taurates and sulfosuccinates.

The amphiphilic compounds according to the invention are thus compounds of the general formula I:

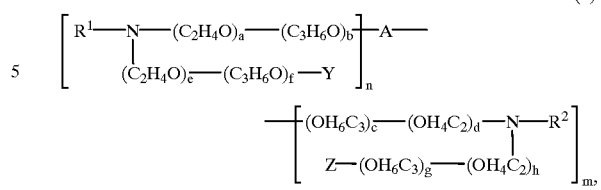

in which $R^1$ and $R^2$, independently of one another, are an unbranched or branched, saturated or unsaturated hydrocarbon radical having from 1 to 22, preferably from 6 to 18, carbon atoms and an unbranched or branched, saturated or unsaturated acyl radical having from 2 to 23, preferably from 7 to 19, carbon atoms, n and m, independently of one another, are at least 1 and the sum of n and m is a number from 2 to 200, preferably from 2 to 100 and particularly preferably from 2 to 10.

a, b, c, d, e, f, g and h are, independently of one another, numbers from 0 to 15, and the sum of a and b, c and d, e and f and g and h must in each case be at least 1. The alkoxide units are incorporated randomly or blockwise, and the sequence is arbitrary. Y and Z. independently of one another, are hydrogen or functional groups. Functional groups which may be mentioned are —CH$_2$COOM, —SO$_3$M, —C$_2$H$_4$SO$_3$M, —C(O)C$_2$H$_3$(SO$_3$M)COOM', —P(O)(OM)$_2$, where M and M' are alkali metal, ammonium, alkanolammonium or ½ alkaline earth metal.

Specific radicals which may be mentioned as substituents $R^1$ and $R^2$ are methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-uneicosyl, n-docosyl and their branched-chain isomers, and the corresponding mono-, di- or triunsaturated radicals and the corresponding acyl compounds.

The spacer A is an aliphatic, cyclic or acyclic or an aromatic di-, oligo- or polycarbonate of the formula II:

R originates from a di-, oligo- or polyol which, preferably, does not tend toward cyclization, in which r hydroxyl groups are esterified with carbonic acid derivatives. r is a number from 2 to 200, preferably from 2 to 20, particularly preferably from 2 to 10. Examples thereof which may be mentioned here are alkylenediols, preferably having from 2 to 8 carbon atoms, di- to tetraethylene glycols, di- to tetrapropylene glycols, polyalkylene glycols, such as, for example polyethylene glycols, oligo- or polyglycerols, sorbitol, polyvinyl alcohol, trimethylolpropane and acetals such as 2,2'-methylene-bis( 1,3-dioxolane-5-methylene)diol. For stoichiometric reasons, r=n+m.

The amphiphilic compounds according to the invention are distinguished by extremely low critical micelle concentrations (CMCs) and very low surface tensions, which must be attributed to their special structure—at least two hydrophilic groups and at least two hydrophobic groups. Furthermore, most of them have a rather high hydrophilic suspension capacity which is about halfway between that of conventional surfactants and that of pentasodium tripolyphosphate. Some of these compounds are extremely rapid wetting agents. They all have very high hardness stability and good solubility in water.

The amphiphilic compounds according to this invention are particularly suitable as emulsifiers, demulsifiers, detergents, dispersants, hydrotropes and antistatics in industry and domestically, for example in the areas of metalworking, ore extraction, textile auxiliaries, surface finishing, plastics processing, washing and cleaning, cleaning of hard surfaces, in particular as a manual dishwashing detergent, cosmetics, medicine and foods processing and preparation.

In these cases they can be combined with all customary anionic, nonionic, cationic and ampholytic surface-active substances.

Examples which may be mentioned of nonionic surface-active substances which can be used for a combination are: fatty acid glycerides, fatty acid polyglycerides, fatty acid esters, ethoxylates of higher alcohols, polyoxyethylene fatty acid glycerides, polyoxy-ethylene/propylene glycol fatty acid esters, polyoxy-ethylene sorbitan fatty acid esters, polyoxyethylene castor oil or hydrogenated castor oil derivatives, polyoxyethylene lanolin derivatives, polyoxy-ethylene fatty acid amides, polyoxyethylene alkylamines, alkanolamines, alkylamine oxides, derivatives of protein hydrolysates, hydroxy-mixed ethers, alkylpolyglycosides, amine oxides and alkylglucamides.

Examples which may be mentioned of anionic surface-active substances which can be used for combinations are: soaps, ether carboxylic acids and salts thereof, alkylsulfonates, α-olefinsulfonates, α-sulfofatty acid derivatives, sulfonates of higher fatty acid esters, higher alcohol sulfates, alcohol ether sulfates, hydroxy-mixed ether sulfates, salts of phosphate esters, taurides, isethionates, linear alkylbenzenesulfonates, cumenesulfonate, alkylarylsulfonates, sulfates of polyoxyethylene fatty acid amides and salts of acylamino acids.

Examples which may be mentioned of customary cationic surface-active substances which can be used for combinations are: alkyltrimethylammonium salts, dialkyldimethylammonium salts, alkyldimethylbenzylammonium salts, alkylpyridinium salts, alkylisoquinolinium salts, benzethonium chlorides and cationic acylamino acid derivatives.

Examples which may be mentioned of ampholytic surface-active substances which can be used for combinations are: amino acids, betaines, sulfobetaines, imidazoline derivatives, soybean oil lipids and lecithin.

Furthermore, the amphiphilic compounds according to the invention can be also be combined together on their own.

It is likewise possible to add conventional additives to the amphiphilic compounds according to the invention. Such additives are specifically selected for a formulation and for example comprise inorganic salts, such as sodium chloride and sulfate, and builders, hydrotropes, UV absorbers, softening agents, chelating agents, viscosity modifiers and fragrances.

The abovementioned compounds can be prepared from di-, oligo- or polycarbonates and at least two equivalents of alkoxylated fatty amines and/or alkoxylated fatty acid amides. The precursors used here are the di-, oligo- or polyols which can be reacted with one equivalent of diethyl carbonate per hydroxyl group. There must be at least two equivalents of diethyl carbonate, in the case of oligo- or polyols the properties of the molecule can be adjusted more exactly by the degree of conversion with carbonate or amine ethoxylate or amide ethoxylate in the last step. Both of the esterification and transesterification reactions described above, can be carried out using known catalysts, such as, for example, titanates, mixtures of antimony trioxide and calcium acetate, stannates, zinc acetate and alkali metal oxides. Titanates have, however, proven to be particularly favorable as regards reaction times and colour quality. The anionic amphiphilic compounds can be prepared by reacting the aforementioned products with, for example, amidosulfonic acid, chloroacetic acid salts, isethionates or maleic anhydride, and neutralizing the resulting mixture with aqueous alkali metal or alkaline earth metal hydroxides, aqueous ammonia or alkanolamines. If required, the products are bleached in aqueous solution with hydrogen peroxide (0.1 to 2.0%, based on solid).

What is claimed is:

1. An amphiphilic compound of the general formula I

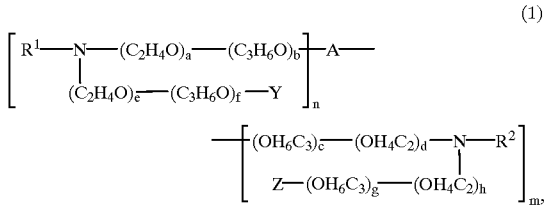

in which $R^1$ and $R^2$, independently of one another, are an unbranched or branched, saturated or unsaturated hydrocarbon radical having from 1 to 22 carbon atoms or an unbranched or branched, saturated or unsaturated acyl radical having from 2 to 23 carbon atoms, A is a di-, oligo- or polycarbonate, and Y and Z are hydrogen or a functional radical —$CH_2COOM$, —$SO_3M$, —$C_2H_4SO_3M$, —$C_2H_4SO_3M$, —$C(O)C_2H_3(SO_3M)COOM'$ or —$P(O)(OM)_2$ where M, M'=alkali metal, ammonium, alkanolammonium or ½ alkaline earth metal, and in which n and m, independently of one another, are each at least 1, the sum of n and m is from 2 to 200 and a, b, c, d, e, f, g and h, independently of one another, are from 0 to 15, and the sum of a and b, c and d, e and f and g and h must in each case be at least 1.

2. The amphiphilic compound as claimed in claim 1, wherein the spacer A satisfies the general formula (II):

wherein R is derived from a di-, oligo- or polyol, and r is a number from 2 to 200.

3. The amphiphilic compound as claimed in claim 2, wherein R is derived from a di-, tri- or polyethylene glycol.

4. The amphiphilic compound as claimed in claim 1, wherein
the hydrocarbon radicals $R^1$ and $R^2$ in the formula I, independently of one another contain from 6 to 18 carbon atoms, and the acyl radicals, independently of one another, contain from 7 to 19 carbon atoms.

5. The amphiphilic compound as claimed in one of claim 1, wherein
Y and Z, independently of one another, are hydrogen or a functional radical —$CH_2COOM$, —$SO_3M$, —$C_2H_4SO_3M$, —$C(O)C_2H_3(SO_3M)COOM'$ or —$P(O)(OM)_2$ where M, M'=alkali metal, ammonium, alkanolammonium or ½ alkaline earth metal.

6. A composition comprising at least one amphiphilic compound of the general formula I as claimed in claim 1.

7. The composition of claim 6, comprising two or more of said amphiphilic compound.

8. A composition comprising at least one amphiphilic compound of the general formula as claimed in claim 1, and a surface active substance selected from the group consisting of anionic, nonionic, cationic and ampholytic surface active substances.

9. A composition comprising a mixture of homologues of at least two amphiphilic compounds of the general formula as claimed in claim 1.

10. In a process of emulsifying, the improvement comprising emulsifying with the amphiphilic compound of claim 1 as the emulsifier.

11. In a process of demulsifing, the improvement comprising demulsifying with the amphiphilic compound of claim 1 as the demulsifier.

12. In a process of metalworking, the improvement comprising metalworking with the amphiphilic compound of claim 1 as a processing auxiliary.

13. In a process of ore extraction, the improvement comprising ore extracting with the amphiphilic compound of claim 1 as a processing auxiliary.

14. In a process of surface finishing, the improvement comprising surface finishing with the amphiphilic compound of claim 1 as a processing auxiliary.

15. In a process of manufacturing plastics, the improvement comprising manufacturing plastics with the amphiphilic compound of claim 1 as a processing auxiliary.

16. In a process of processing plastics, the improvement comprising processing plastics with the amphiphilic compound of claim 1 as a processing auxiliary.

17. In a process of cleaning or washing textiles, the improvement comprising cleaning or washing textiles with the amphiphilic compound of claim 1 as a textile auxiliary.

18. In a process of cleaning hard surfaces, the improvement comprising cleaning hard surfaces with the amphiphilic compound of claim 1 as a cleaning material.

19. In a process of manual dishwashing, the improvement comprising manually dishwashing with the amphiphilic compound of claim 1 as a cleaning material.

20. In a process of cleaning or washing skin or hair, the improvement comprising cleaning or washing skin or hair with the amphiphilic compound of claim 1 as a cleaning material.

* * * * *

UNITED STATES PATENT AND TRADEMARK OFFICE
CERTIFICATE OF CORRECTION

PATENT NO. : 6,066,755

DATED : May 23, 2000

INVENTOR(S): Herbert KOCH, et al.

It is certified that an error appears in the above-identified patent and that said Letters Patent is hereby corrected as shown below:

Column 4, line 52, "claimed in one of claim" should read --claimed in claim--.

Signed and Sealed this

Seventeenth Day of April, 2001

Attest:

NICHOLAS P. GODICI

Attesting Officer

Acting Director of the United States Patent and Trademark Office